(12) United States Patent
Luemkemann et al.

(10) Patent No.: US 6,514,240 B2
(45) Date of Patent: Feb. 4, 2003

(54) ADAPTER FOR OPHTHALMOLOGIC EQUIPMENT

(75) Inventors: Frank Luemkemann, Jena; Eberhard Hofmann, Bollberg, both of (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/860,348

(22) Filed: May 17, 2001

(65) Prior Publication Data

US 2002/0029033 A1 Mar. 7, 2002

(30) Foreign Application Priority Data

May 23, 2000 (DE) .......................................... 100 25 843

(51) Int. Cl.$^7$ ............................................... A61B 18/18
(52) U.S. Cl. ............................... 606/4; 606/10; 351/200
(58) Field of Search .............................. 606/1, 2, 4, 10, 606/13, 17; 351/200, 208, 214

(56) References Cited

U.S. PATENT DOCUMENTS 3,944,342 A * 3/1976 Martinez .................... 351/206
4,331,392 A * 5/1982 Sato ........................... 351/214
5,634,923 A * 6/1997 Brenner et al. ............. 351/213

FOREIGN PATENT DOCUMENTS

DE 42 27 390 C2 6/1994
DE 94 08 098 8/1994

OTHER PUBLICATIONS

English Abstract of DE 42 27 390 C2.
English Abstract of G 94 08 098.4.

* cited by examiner

Primary Examiner—Teresa Walberg
Assistant Examiner—Thor Campbell
(74) Attorney, Agent, or Firm—Reed Smith LLP

(57) ABSTRACT

An adapter for connecting and releasably and rigidly positioning a laser link on the housing of different slit lamp microscopes comprising a base, a fastening device on one end for fastening to a housing of a slit lamp microscope, a coupling device for coupling the laser link to the housing of the slit lamp microscope in a releasable and rigid manner, the coupling device for complementary engagement with a coupling device on the laser link.

11 Claims, 5 Drawing Sheets

ADAPTER FOR OPHTHALMOLOGIC EQUIPMENT

BACKGROUND OF THE INVENTION a) Field of the Invention

The invention is directed to an adapter for ophthalmologic equipment, in particular for equipment for photodynamic therapy (PDT) or for laser coagulation in the eye, the adapter being provided for the defined fastening and positioning of a laser link on slit lamp microscopes.

For such equipment, the laser link is used for introducing the radiation usually supplied via light conductors from distant laser radiation sources into the eye of the patient and for directing or splitting off light for the observation of the interior of the eye into the observation ray path of the slit lamp microscope.

b) Description of the Related Art

From U.S. Pat. No. 5,954,711, the provision of a fixed arm for a laser coagulation device (laser link) is known, wherein this fixed arm has means for connecting this device in a precisely defined relative position to the housing of the slit lamp microscope. This laser link is used for introducing laser radiation for coagulation into the eye of the patient and for positioning it at the places to be irradiated in the eye.

The disadvantage of this device is the fact that attaching the laser link and exchanging the same is not possible for different slit lamp microscopes, since a separate link must be provided for each different combination of equipment (link-slit lamp) because of the arm that is permanently attached to the link.

From the in-house print publication "Laser Spot delivery Devices for the OcuLight SL/SLx" of the company Optomed Corp., 733 North Shoreline Blvd. Mountain View, Calif. 94043, USA, the provision of a transition piece between a laser link and a slit lamp microscope which is adjustably connected by means of a dovetail joint with the link is known. The transition piece comprises means for setting and adjusting the mutual positions of the respective parts and is therefore of a complicated construction and expensive to produce.

OBJECT AND SUMMARY OF THE INVENTION

It is therefore the primary object of the invention to create exchangeable adapters for ophthalmologic equipment with which the exchangeability of a link and different slit lamp microscopes is made possible while maintaining an intended and defined relative position of a link and a slit lamp microscope.

According to the invention, this object is met by an adapter for ophthalmological equipment for the defined connection and positioning of a laser link on the housing of different slit lamp microscopes which comprises a base body, on the one end of which fastening means are provided for fastening it to a housing of a slit lamp microscope in a manner that is positionally aligned, releasable and has no play. On the other end of the base body and contiguous to the laser link, first means of coupling or coupling elements and/or position securing elements are provided for coupling the laser link to the housing of the slit lamp microscope in a manner that is positionally aligned, releasable and has no play. These first coupling means can be engaged in a rigid and yet releasable operative connection with matching complementary second coupling means.

Thus, the adapter for ophthalmologic equipment for the defined connection and positioning of a laser link on the housing of different slit lamp microscopes has a base body on the one end of which fastening means are provided for fastening it to the housing of a slit lamp microscope in a manner that is positionally aligned, releasable and has no play, and on the other end of which contiguous to the laser link first means of coupling or coupling elements and/or position securing elements are provided for coupling the laser link to the housing of the slit lamp microscope in a manner that is positionally aligned, releasable and has no play. These first coupling means can be engaged in a rigid and yet releasable operative connection with matching complementary second coupling means.

It is thus advantageous if at least the one fastening means is or the more than one fastening means are adjustable along one axis relative to the base body.

An advantageous connection results when the first and second coupling means are frictionally and positively locked, the positively locking connection being used for the mutual positional alignment and the frictionally locking connection for the rigid and yet releasable coupling of the parts to be connected to each other.

The first coupling means of the base body and the second coupling means of the laser link are coupled to each other with a releasable connection so that the exchangeability of the laser link and the connection of a laser link with varying slit lamp microscopes can be realized.

It is also advantageous if a positively locking connection is provided for the positional alignment of the laser link on the base body of the adapter and if a rigid and yet releasable frictionally locking connection is provided for the fixing of the base body to the laser link. For this purpose, a screw or bayonet connection that is by itself known could simply be provided between the base body and the laser link.

It is also advantageous if a positively locking connection is provided between base body and laser link by means of which relative movement of the two parts connected with each other is avoided.

It is furthermore advantageous if the one or more fastening means arranged on the base body of the adapter with which the adapter can be coupled to the housing of the slit lamp microscope can be adjusted or positionally altered with at least one degree of freedom to attain a precisely defined mutual position of the connected parts.

It is advantageous if the fastening means is connected to the base body of the adapter by a joint which permits the rotation of the base body relative to the fastening means on one axis so that the laser link, which is coupled to the base body of the adapter by use of the first and second coupling means, can be removed from the ray path of the slit lamp microscope. Advantageously, means are provided at the endpoints of the rotation range of the base body which bring the latter into a defined position relative to the fastening means and fix it in its position by applying force. Suitable for this purpose is, for example, a catch of a type that is known as such which consists of a catch element which has a force applied to it and a groove. The force can, for example, be generated by a spring.

BRIEF DESCRIPTION OF THE DRAWINGS

The invention is to be described in more detail below by means of an embodiment example. In the accompanying drawings.

DESCRIPTION OF THE PRFERRED EMBODIMENTS

Figure 1:
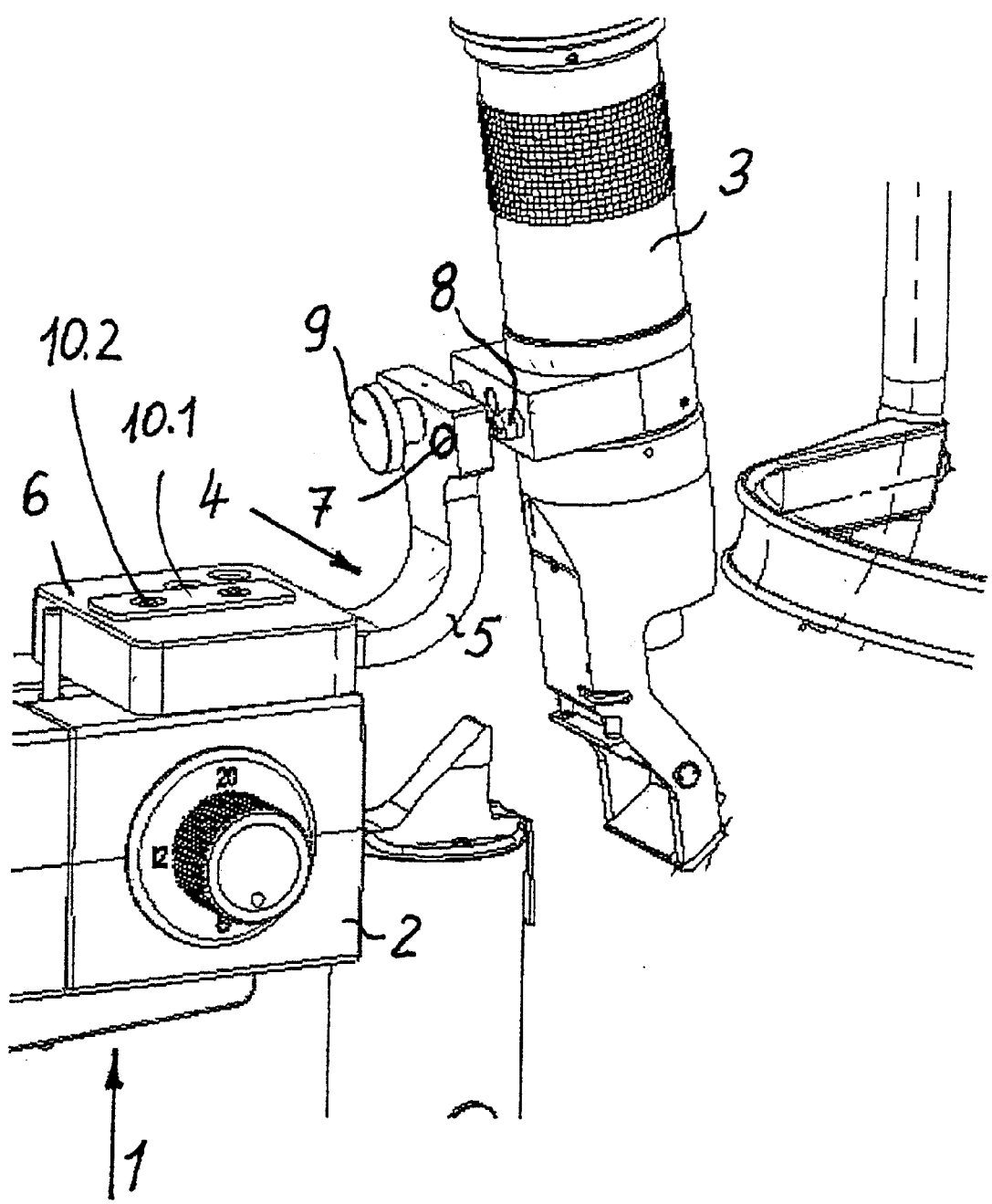
FIG. 1 shows a slit lamp microscope with an adapter and a laser link.

In FIG. 1, an slit lamp microscope 1 with a housing 2 and a laser link 3 is illustrated in a perspective drawing wherein the connecting part between the laser link 3 and the housing 2 is represented as an adapter 4. The adapter 4 includes a base body 5 on which a fastening means 6 is provided on the end facing the housing 2 of the slit lamp microscope 1 by means of which it can be connected with the housing 2 in a manner that is positionally aligned, releasable and has no play. On the end of the base body 5 that faces the laser link 3, first means of coupling 7 or coupling elements as well as position securing elements 9 are provided for coupling the laser link 3 to the adapter 4 in a manner that is positionally aligned, releasable and has no play, these first coupling elements 7 being in a rigid, positively and frictionally locking operative connection with matching complementary second coupling means 8 arranged on the laser link 3. The position securing elements 9, represented here, for example, as a screw which is screwed into a matching inside thread in the laser link 3, are used for the realization of a rigid and yet releasable frictionally locking connection between the aforementioned parts. Such a frictionally locking connection can also be realized as a bayonet connection (not shown). Both types of connection have the advantage of being realizable quickly without recourse to additional aids.

Thus, the positively locking connection of the second means of coupling 8 with the first means of coupling 7 realized as a bore hole 7.2 and an elongated hole 7.1 (FIG. 3) is used for the positional alignment of the laser link 3 on the base body 5 of the adapter 4. By means of the additional positively locking connection between the base body 5 and the laser link 3, a relative movement of the two parts connected to each other is prevented. Instead of pin and borehole as shown in the figures, other suitable elements, like feather key and groove, or toothed profiles and polygons with counterparts that are shaped correspondingly, can be used.

The fastening means 6, arranged on the end of the base body 5 facing the slit lamp microscope 1, is arranged on the base body 5 so that it can be adjusted along the line of its lengthwise extent and therefore with one degree of freedom. For this purpose, corresponding position altering and/or locking elements 10. 1, 10.2, for example the combination of elongated hole/pin and screw in the separate parts to be connected (FIG. 3), are provided.

For the securing in position of the fastening means 6 on the housing 2 of the slit lamp microscope 1, studs or pins 11.1, 11.2 are provided on the bottom side which engage in corresponding boreholes (not shown) on the housing 2. For attaining the rigid and yet releasable connection, a screw 12 (FIGS. 3, 5, 6) or another suitable element is used.

To remove the laser link 3 from the adapter 4, the screw 9 is simply released and the laser link 3 can be removed. Attaching the laser link 3 is done by engaging the first means of coupling 7.1, 7.2 and the second means of coupling 8 in an operative connection and by fixing the connection for good by tightening the screw 9.

Figure 2:
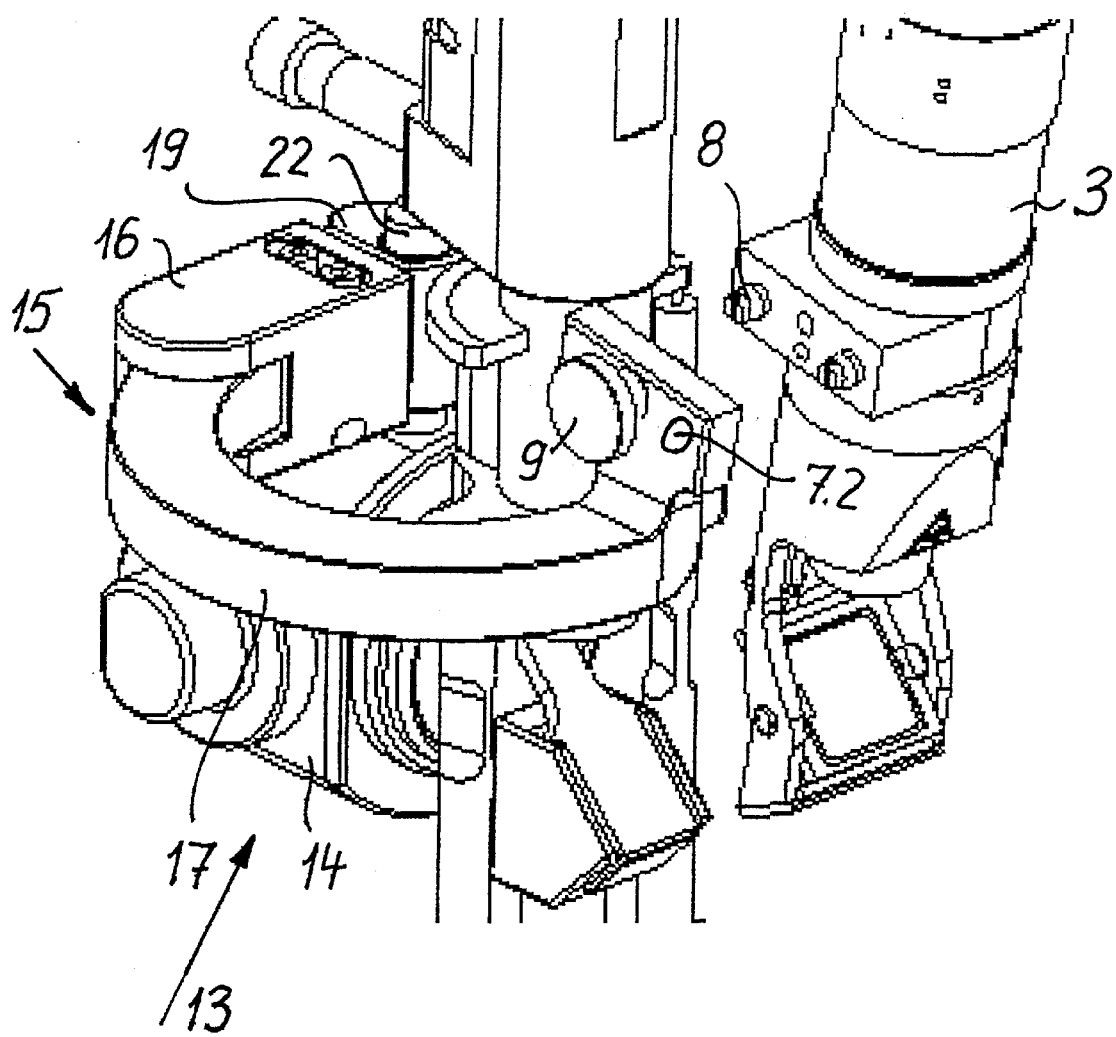
FIG. 2 shows a slit lamp microscope with a pivotable adapter and a laser link.
Figure 7:
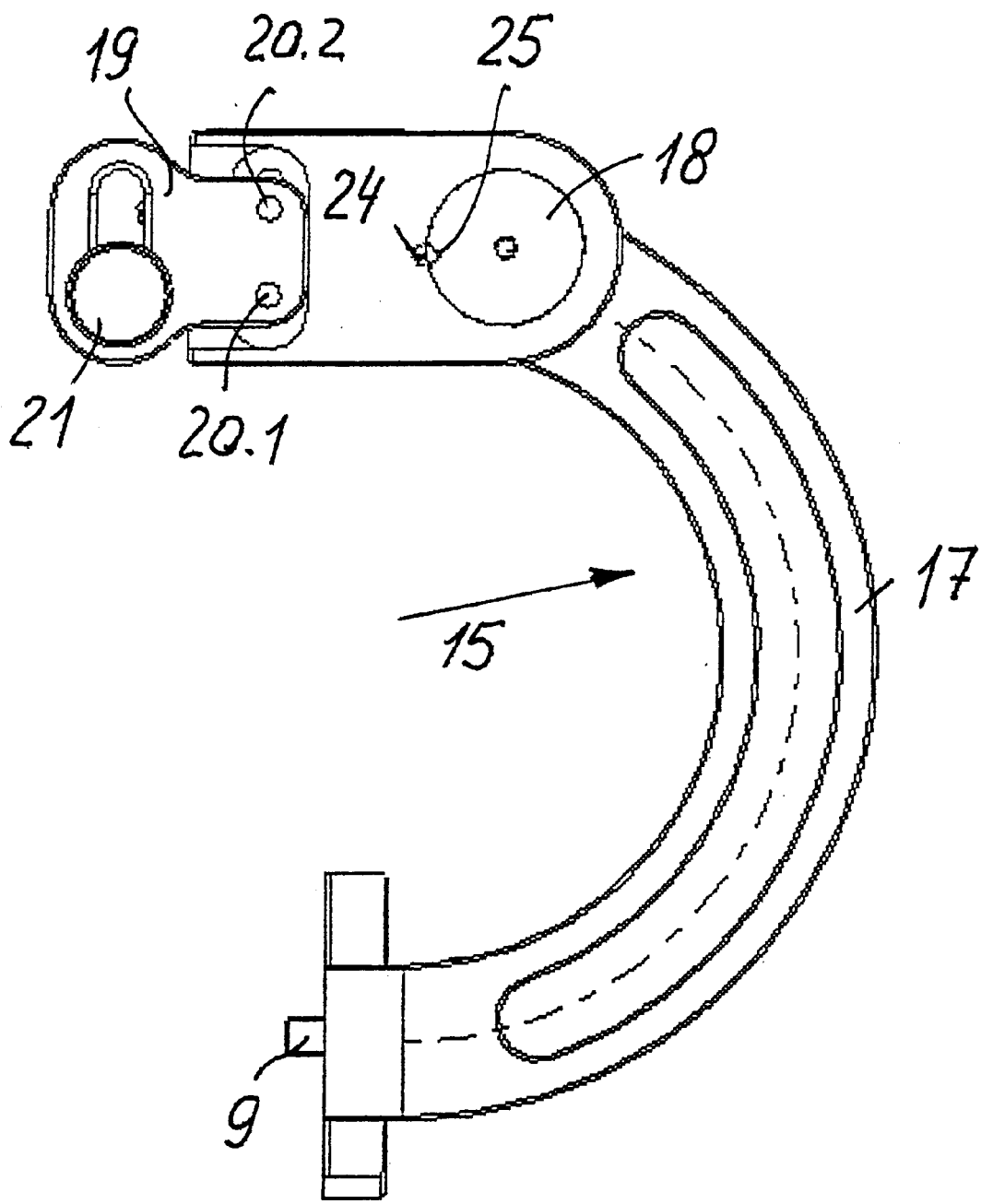
FIG. 7 shows a view from below onto the adapter according to FIG. 4.

FIG. 2 shows a further embodiment form of a slit lamp microscope 13, on the housing 14 of which an adapter 15 is arranged which comprises a means of fastening 16, a base body 17, first means of coupling 7.1, 7.2 and position securing elements 9. The first means of coupling 7.1, 7.2 and the position securing elements 9 have the same references in this FIG. 2 because they are constructionally identical to those in FIG. 1. The base body 17 is connected to the fastening means 16 by a joint, which makes possible a rotation or pivoting of the base body 17 relative to the fastening means 16 on a joint axle 18 (FIG. 7). In this manner, the removal of the laser link 3 attached to the base body from the ray path of the slit lamp microscope 13 is realized. Coupling and fastening the laser link 3 to the housing 14 of the slit lamp microscope 13 is done in the manner described in connection with FIG. 1.

Figure 4:
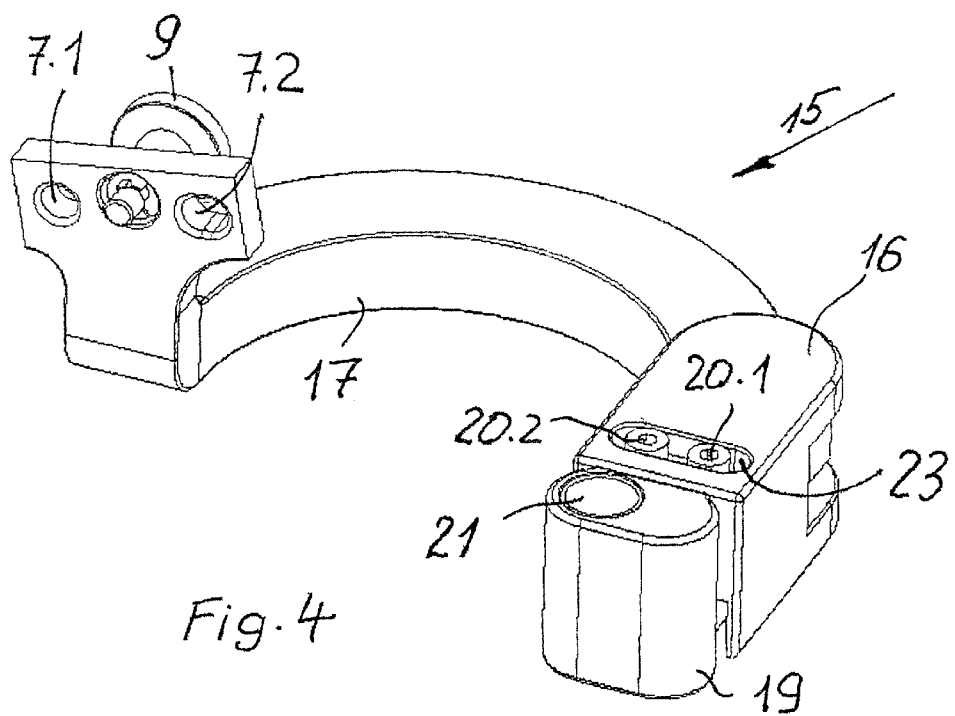
FIG. 4 shows an adapter with a pivotable base body.

The fastening means 16 shown in combined effect with the slit lamp microscope 13 and the laser link 3 in FIG. 2 and shown in perspective and from underneath in FIGS. 4 and 7 comprises a coupling part 19 which has elements for coupling it to the housing 14. The position of this coupling part 19 can be altered and adjusted in one direction relative to the rest of the part of the fastening means 16 receiving the axle of the joint 18. A combination of corresponding position-altering and/or locking elements 20.1 and 20.2 is provided in a simple fashion, for example by the combination of elongated hole/pin and screw in the individual connected parts. The adapter 15 is pushed with its bore onto a journal (FIG. 2) of the housing 14 and connected to the housing 14 by means of further position securing elements (not shown).

Figure 3:
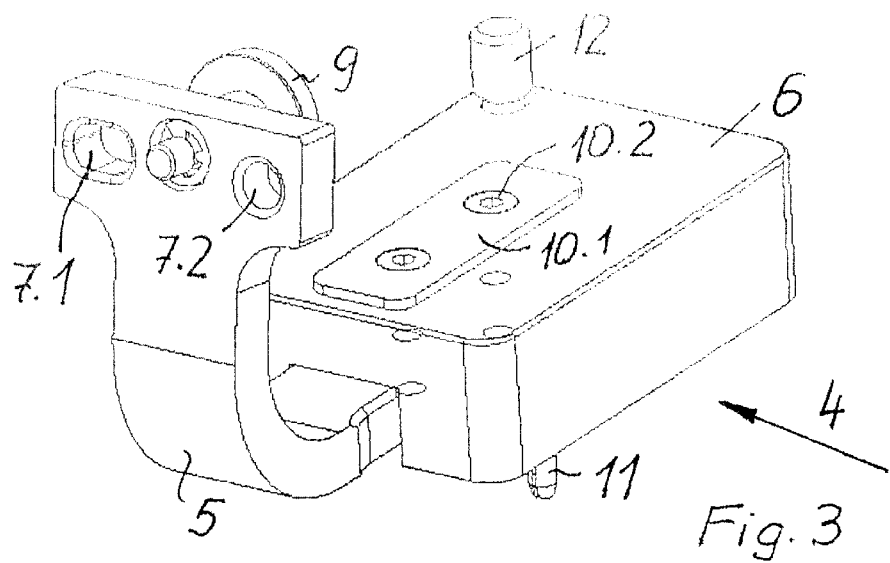
FIG. 3 shows an adapter with a base body and fastening means.

FIG. 3 shows a perspective view of an embodiment form of an adapter 4 with a base body 5 and fastening means 6, wherein on the base body 5 first coupling means 7.1, 7.2 comprising an elongated hole 7.1 and a borehole 7.2 and a screw as a position securing element 9 are provided.

A further embodiment form of an adapter 15 which can be pivoted on one axis in one plane is shown in FIG. 4. This adapter 15 includes a base body 17 which has the first coupling means 7.1, 7.2 (elongated hole and borehole) and a screw as a position securing element 9 on its one end where the laser link 3 (FIG. 2) is attached. The fastening means 16 is arranged on its other end which has a coupling part 19 with a borehole 21 with which it can be pushed onto a journal 22 on the housing 14 of the slit lamp microscope 13 (FIG. 2). The coupling part 19 is connected with the fastening means by locking elements 20.1, 20.2 (FIG. 7) in such a manner that an adjustment of the parts connected to each other can be realized with at least one degree of freedom (in one direction). When the locking elements 20.1, 20.2 represented as screws in FIG. 4 have been released, the coupling part 19 can be moved by a small amount along the lengthwise extent of an elongated hole 23 and relative to the fastening means 16, and the mutual position of the parts can therefore be adjusted.

The base body 17 is hinged in the fastening means 16 so that it can be pivoted on a joint axle 18 (FIG. 7) to enable the removal of the laser link 3 attached to the adapter 15 from the ray path of the slit lamp microscope 13. Means are provided for the realization of a defined and fixed final position of the pivoting range of the base body 17 where the laser link 3 has to be arranged in the ray path of the slit lamp microscope 13, for example in the shape of a catch of a type that is known as such, which consists of a catch element 24, which has a force applied to it, and a groove 25 (FIG. 7). The force can, for example, be generated by a spring or in another manner, for example also magnetically.

Figure 5:
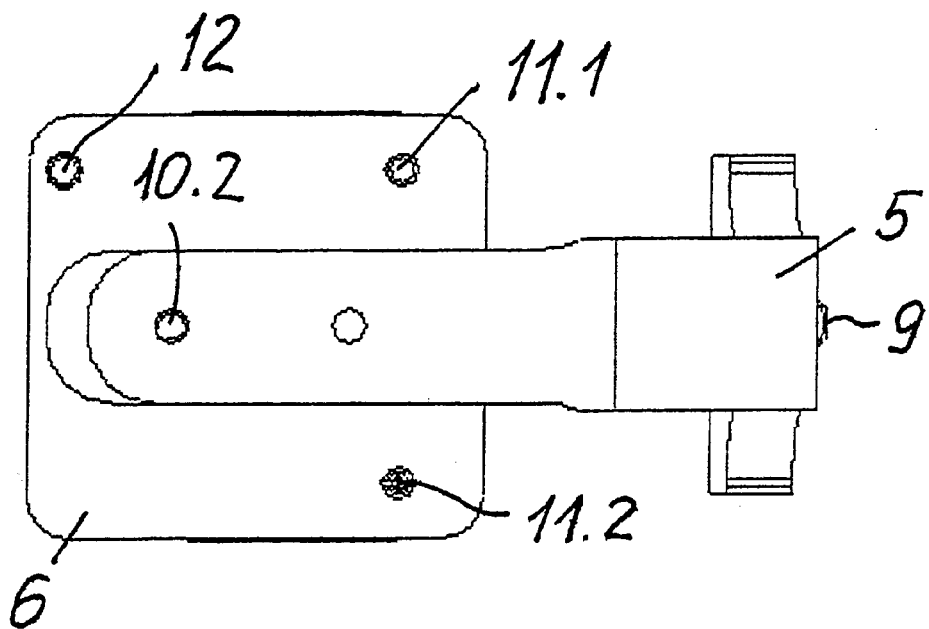
FIG. 5 shows a view from below onto the adapter according to FIG. 3.
Figure 6:
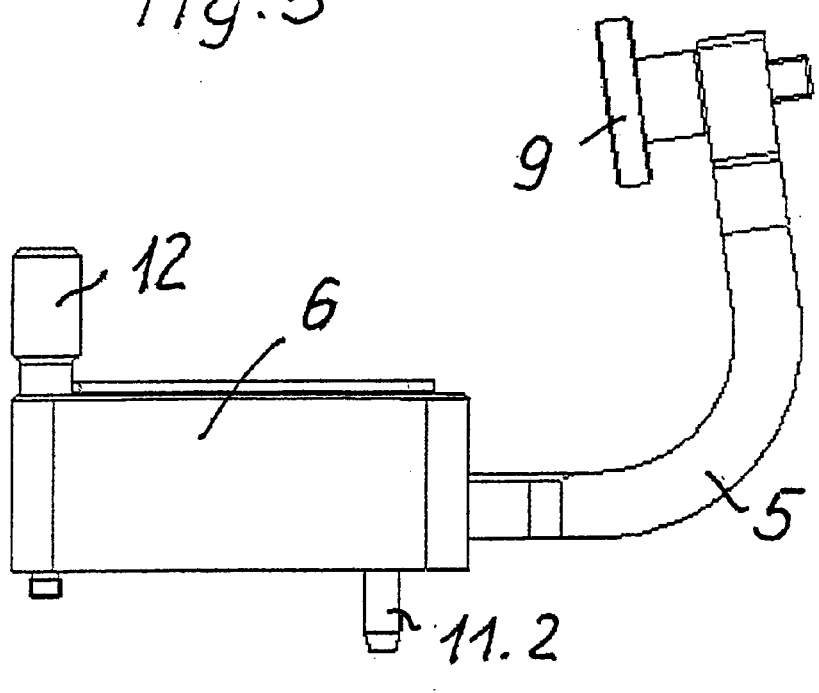
FIG. 6 shows a side view of the adapter according to FIG. 3.

In the case of the adapter 4 as it is used according to the arrangement in FIG. 1 and shown in different views in FIGS. 5 and 6, several pins or studs are provided which protrude from the surface of the fastening means 6 that faces the housing 2 of the slit lamp microscope 1; they are inserted into matching boreholes of the housing 2 for the purpose of positionally fixing the connected parts. For fixing the connected parts, a screw 12 is provided in the fastening means 6 which is screwed into a matching thread of the housing 2.

While the foregoing description and drawings represent the present invention, it will be obvious to those skilled in the art that various changes may be made therein without departing from the true spirit and scope of the present invention.

What is claimed is:

1. An adapter for ophthalmologic equipment for the defined connection and positioning of a laser link on the housing of different slit lamp microscopes comprising:
   a base body;
   on one end of said body, fastening means are provided for fastening it to a housing of a slit lamp microscope in a manner that is positionally aligned, releasable and has no play;
   on the other end of said base body and contiguous to the laser link, first means of coupling or coupling elements and/or position securing elements being provided for coupling the laser link to the housing of the slit lamp microscope in a manner that is positionally aligned, releasable and has no play; and
   wherein said first coupling means can be engaged in a rigid and yet releasable operative connection with matching complementary second coupling means.

2. The adapter according to claim 1, wherein at least said one fastening means is adjustable along at least one axis relative to the base body.

3. The adapter according to claim 2, wherein more than one fastening means are adjustable along at least one axis relative to the base body.

4. The adapter according to claim 1, wherein the first and second coupling means are frictionally connected and in a positive lock.

5. The adapter according to claim 1, wherein the first coupling means of the base body and the second coupling means of the laser link are coupled to each other with a releasable connection.

6. The adapter according to claim 1, wherein a positively locking connection for the positional alignment and fixing of the laser link on the base body of the adapter and a rigid and yet releasable frictionally locking connection for fixing the base body to the laser link are provided.

7. The adapter according to claim 1, wherein the frictionally locking connection between base body and laser link is a screw or bayonet connection.

8. The adapter according to claim 1, wherein a positively locking connection is to be provided between base body and laser link by which relative movement of the two parts connected with each other is prevented.

9. The adapter according to claim 1, wherein one or more fastening means arranged on the base body of the adapter can be adjusted or positionally altered with at least one degree of freedom.

10. The adapter according to claim 1, wherein the fastening means is connected to the base body of the adapter by a joint which permits the rotation of the base body relative to the fastening means on one axis.

11. The adapter according to claim 10, wherein means are provided at least at one endpoint of the rotation range of the base body which bring the latter into a defined position relative to the fastening means and fix it in this position by applying force.

* * * * *